United States Patent [19]

Kroyer

[11] Patent Number: 5,622,584
[45] Date of Patent: Apr. 22, 1997

[54] METHOD OF PRODUCING FLOW LINES IN A SANITARY PRODUCT

[76] Inventor: Karl K. K. Kroyer, Le Vieux Moulin, 12, rue de la Libération, F-06520 Magagnosc, France

[21] Appl. No.: 502,013

[22] Filed: Jul. 13, 1995

Related U.S. Application Data

[63] Continuation of Ser. No. 141,927, Oct. 28, 1993, abandoned.

[51] Int. Cl.$^6$ ............... A61F 13/20; A61F 13/52
[52] U.S. Cl. ............... 156/209; 156/281; 264/284; 604/378; 604/380; 27/275; 27/276; 27/278
[58] Field of Search .................. 156/209, 281; 604/378–382; 264/284; 427/275, 276, 277, 278, 288

[56] References Cited

U.S. PATENT DOCUMENTS

| | | | |
|---|---|---|---|
| 3,934,588 | 1/1976 | Mesek et al. | 604/378 X |
| 4,077,410 | 3/1978 | Butterworth et al. | 604/378 X |
| 4,211,227 | 7/1980 | Anderson et al. | 604/380 X |
| 4,585,449 | 4/1986 | Karami | 604/378 |
| 4,655,757 | 4/1987 | McFarland et al. | 604/378 X |
| 4,820,294 | 4/1989 | Morris | 604/378 X |
| 4,865,596 | 9/1989 | Weisman et al. | 604/368 |
| 4,923,454 | 5/1990 | Seymour et al. | 604/368 |
| 5,009,651 | 4/1991 | Kamishioiri et al. | 604/378 |
| 5,156,902 | 10/1992 | Pieper et al. | 604/378 X |

*Primary Examiner*—Jeff H. Aftergut
*Attorney, Agent, or Firm*—Watson Cole Stevens Davis, P.L.L.C.

[57] ABSTRACT

A method of making sanitary products giving a high wearing comfort includes the step of forming three superposed interconnected layers (14, 15, 16). The outer layers (14, 16) are made of hydrophobic fibers and the intermediate layer (15) is made of hydrophilic fibers. The top sheet of the sanitary product is constructed of the layer (16), and has flow lines throughout the layer. The flow lines are made by an embossing roller (21) having a pattern of raised ridges. The ridges are provided with a wetting agent which, when applied to the front sheet (16), neutralizes the hydrophobicity of the fibers and provides a pattern of hydrophilic flow lines which allow a body liquid to flow through the top sheet (16).

6 Claims, 3 Drawing Sheets

METHOD OF PRODUCING FLOW LINES IN A SANITARY PRODUCT

This is a continuation of application Ser. No. 08/141,927 filed Oct. 28, 1993, now abandoned.

BACKGROUND OF THE INVENTION

This invention concerns a method for production of a sanitary product comprising three interconnected layers, viz. a liquid impervious back sheet, a liquid impervious front sheet, and a liquid pervious core. More specifically the invention concerns a method for producing such product by means of a plant used for making multi-ply paper. The sanitary products in question might be diapers, sanitary napkins and the like.

It is customary to manufacture sanitary products having the liquid impervious back sheet and front sheet made of elastomer sheets and to have the liquid pervious absorbent core comprising a fibrous material interspaced between the front sheet and back sheet. The front sheet and back sheet are sealed along the marginal edge in order to contain the absorbent core in a secure way. In such products it is possible to establish flow lines or flow areas by providing through going holes in the front sheet.

The prior art product would suffer from several drawbacks. As rather narrow sealings are used along the marginal edge there is a risk that the sealing is broken whereby the absorbent core might fall out. There will be a need for correct positioning of the products. A highspeed production of the product is difficult to obtain.

The final product will give the user a poor wearing comfort due to the elastomer front sheet. Moreover, the final product would have a thickness which could be rather large.

It is an object of the present invention to provide a method making it possible to remedy the drawbacks of the prior art methods thereby providing sanitary products giving a high degree of wearing comfort and which are very thin and have a soft and pleasant front sheet for contact with the user.

Moreover, it is an object of the present invention to provide a method making it possible to manufacture the sanitary product in a plant intended for making multi-ply paper. A not limiting example of such plant for dry forming several fibrous layers on a forming surface has been disclosed in U.S. Pat. No. 3,976,412.

According to the present invention a method is provided for the manufacture of the above-mentioned sanitary product wherein the liquid impervious back sheet and front sheet are made of hydrophobic fibers whereas the liquid pervious core is made of hydrophilic fibers, wherein the hydrophobic front sheet is prepared by a striking roller having a pattern of raised ridges whereto a wetting agent is applied for neutralizing the hydrophobicity of the fibers in the hydrophobic front sheet thereby providing a pattern of flow lines being hydrophilic and allowing for a liquid flow through the front sheet.

As the three layers are provided by a fiber laying it is possible to use three successive fiber distributors in a paper manufacturing plant when making the sanitary product. The application of wetting agent according to any pre-selected pattern is easily effected by use of the striking roller.

According to a preferred embodiment it is possible to use an embossing roller as a striking roller. It is customary to have an embossing or pressure roller arranged following the fiber distributors in a plant for dry-laying of paper. Accordingly, only very small modifications are required in the plant when using an embossing roller it is possible to provide grooves thereby enhancing the wearing comfort of the product as the wetting agent is provided in the bottom of said grooves. Thus a fluid will be directed against the bottom of the grooves and thus in direction of the flow lines. Accordingly, such product would provide a surface for contact with the user which is completely dry due to the hydrophobic fibers in all areas outside the grooves.

Moreover, the use of an embossing roller will compress the fibers in the flow lines. Due to the intimate contact between the hydrophilic fibers in the front sheet and in the core the liquid guidance or the wicking effect becomes more efficient. Thus any liquid would immediately be guided to the absorbent core thereby very quickly leaving the contacting surface of the front sheet dry.

There will be no risk that the individual layers are separated. As the layer is made by following fiber distributors in a paper-making plant the product will have a coherence corresponding to that of multiply papers being manufactured by application of several layers. Thus there will be a bonding between the layers over the total area. Accordingly, it is not necessary to rely on a connection in the marginal area only.

According to a preferred embodiment the embossing roller is manufactured in such a way that the pattern of flow lines are provided in limited areas which are intended for a preselected position in the final sanitary product. Thus it is possible to provide the pattern in an area which is especially suited for the specific sanitary product. Thereby the wearing comfort is enhanced as liquids might be guided through the front sheet in an area of the sanitary product arranged facing against a discharge opening for the body fluid in question.

According to an especially preferred embodiment superabsorbents are admixed to the hydrophilic fibers of the absorbent core. Hereby the absorbing capacity is increased whereby also the wearing comfort is increased. Thus the risk that any fluid will leak out from the absorbent core is obviated even if a large amount of liquid has been absorbed.

According to a further embodiment the superabsorbents are provided only in areas which are intended for a preselected position in the final sanitary product. Hereby it is possible to obtain sanitary products being especially suited for different use, e.g. as diapers for boys and diapers for girls.

According to a further embodiment it is possible to spray the penetrant onto the surface of the hydrophobic front sheet by a series of nozzles. However, the use of a striking or embossing roller is preferred. When using nozzles being guided for providing the wetting agent in a pre-selected pattern of flow lines it is possible to use a computer control. This makes it possible to change the production very quickly in order to manufacture sanitary products having different pattern of flow lines. Thus, it will be possible in the same plant to manufacture diapers for boys and diapers for girls without the need of exchanging any mechanical components of the plant.

In general it will be very easy to feed three successive distributors with different types of cellulosic fibers being pre-treated in order to provide hydrophobic fibers and hydrophilic fibers for the different layers.

The fibers to be used in the present invention comprise cellulosic fibers, wood fibers, mixtures with synthetic fibers including bicomponent fibers and synthetic fibers. The synthetic fibers may, e.g., be of polypropylene or polyethylene. Also, glass fibers, rock wood fibers, and pretreated fibers may be used.

Further features and advantages of the present invention will be understood by reference to the attached drawings taken in conjunction with the ensuing discussion.

DESCRIPTION OF THE PREFERRED EMBODIMENTS

Figure 1:
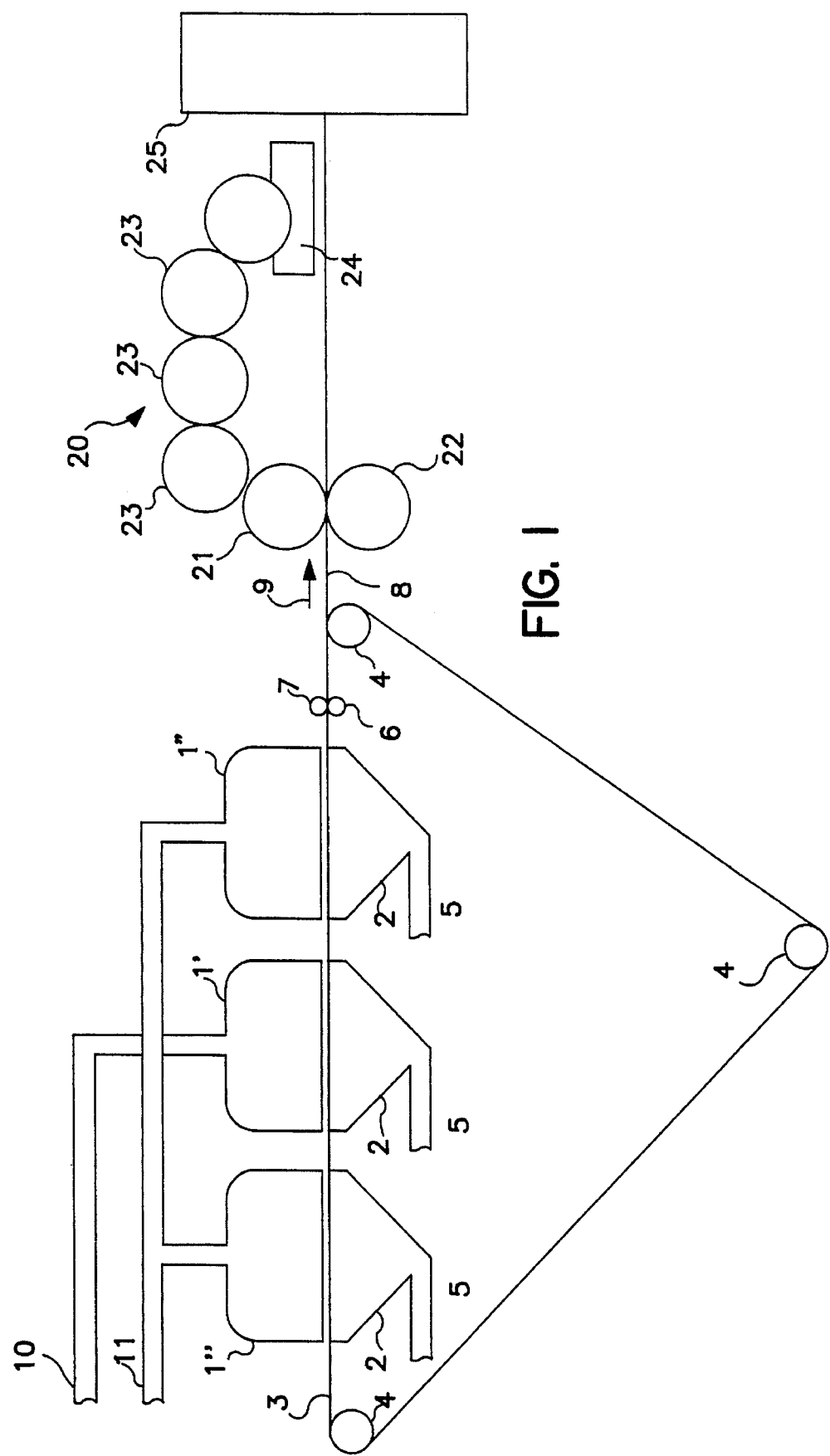
FIG. 1 is a schematic view of an apparatus for use in a method according to the invention.
Figure 2:
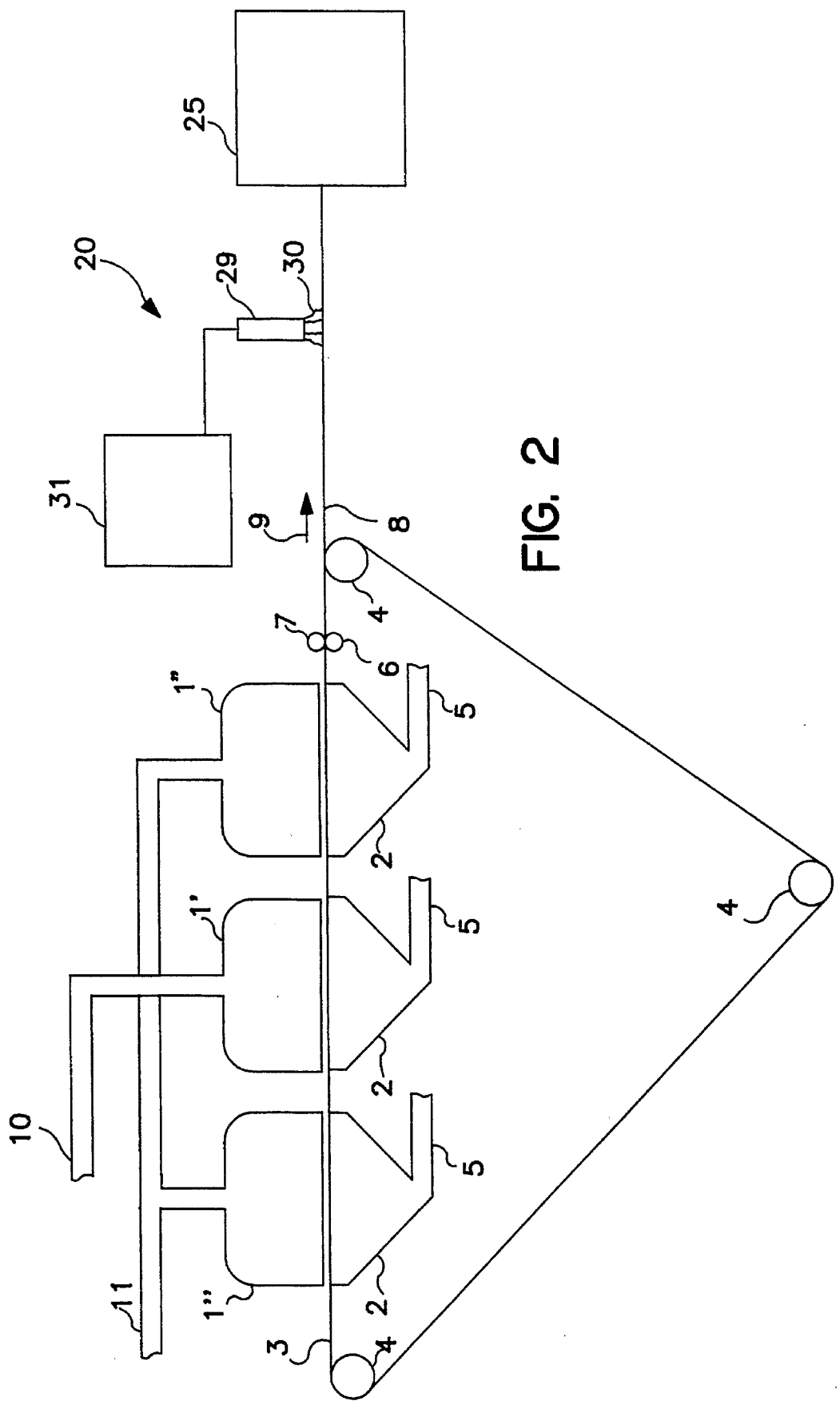
FIG. 2 is a schematic view corresponding to FIG. 1, however, illustrating a further embodiment of an apparatus.

Preferred embodiments for an apparatus for use in a method according to the present invention are schematically illustrated in FIGS. 1 and 2. In these Figures identical or corresponding elements are designated with the same reference numbers and will only be explained in details in connection with FIG. 1.

The apparatus includes three fiber distributors 1 and three suction boxes 2. An endless foraminous forming wire 3 passes therebetween. The forming wire 3 consists e.g. of a mesh net constructed using bronze wires. The forming wire 3 is guided on rollers 4 and is driven by driving means which are not shown. Each of the suction boxes 2 is connected with a suction pipe 5 which is connected to a fan (not shown) for creation of a vacuum therein. The forming wire 3 passes through the nip of a pair of rollers 6, 7 thereby providing a compression of the web 8. The fibrous web 8 is advanced according to an arrow 9.

The intermediate fiber distributor 1' is connected with a supply pipe 10 in order to supply fibers, preferably cellulosic fibers being pre-treated thereby making the fibers hydrophilic. The two outermost distributors 1" are connected with a supply pipe 11 through which fibers are supplied to the outermost distributors 1". These fibers are cellulosic fibers pre-treated in order to make them hydrophobic.

As it occurs from FIG. 1 the web 8 formed in the apparatus comprises two outermost layers consisting of hydrophobic fibers and an intermediate layer of hydrophilic fibers.

Figure 3:
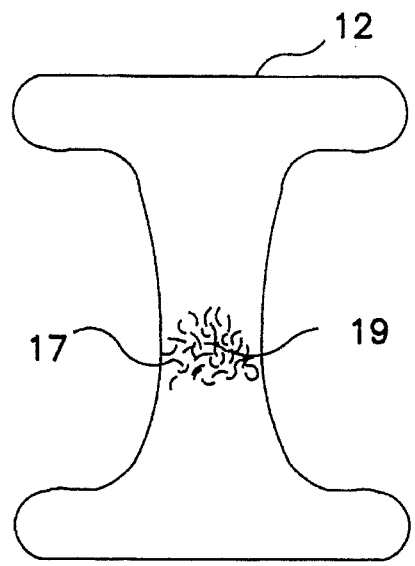
FIGS. 3 and 4 show schematically two embodiments of a sanitary product manufactured by a method according to the invention, and FIG. 5 a partially enlarged cross-sectional view through a product manufactured by a method according to the invention.
Figure 4:
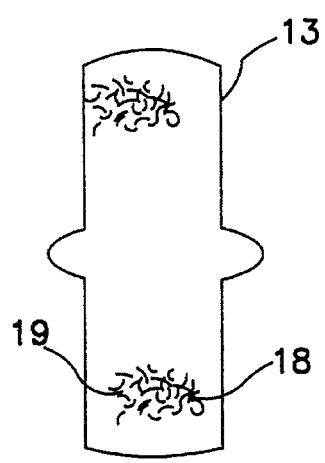

The web 8 is used for the manufacture of a sanitary product 12, 13 (See FIGS. 3 and 4). The sanitary product 12, 13 comprises a back sheet 14, an intermediate layer 15 and a top sheet 16 intended to be in contact with a user (See FIG. 5). The top sheet 16 and the back sheet 14 which consist of the hydrophobic fibers will be liquid impervious as it is known from ordinary diapers, sanitary napkins etc. The intermediate layer 15 consisting of the hydrophilic fibers is liquid pervious or absorbent as known from the absorbent core of ordinary diapers, sanitary napkins, etc. In order to make the sheet 8 formed suitable for use as a sanitary napkin a pattern 17, 18 (See FIGS. 3 and 4) of flow lines 19 is made in the top sheet 16.

This pattern 17, 18 of flow lines 19 may be provided in selected areas as illustrated in FIGS. 3 and 4. Alternatively, it is possible to provide the flow lines 19 across all the surface of the product formed.

The flow lines 19 are provided by use of means 20 for providing flow lines, to be explained in more detail below.

FIG. 1 illustrates the means 20 for providing flow lines in the form of a roller 21 cooperating with a pressure roller 22 on the opposite side of the web 8. The roller 21 is through a series of rollers 23 supplied with a wetting agent from a reservoir 24. The wetting agent is transferred to the roller 21 which is an embossed roller having a pattern of raised ridges (not shown in detail) corresponding to the pattern of flow lines 19 which are intended to provided in the web 8. The roller 21 might be a striking roller which does not exert an embossing in the web 8. However, it is preferred that the roller 21 is urged against the pressure roller 22, so that an embossing of the web is performed simultaneously with the application of the wetting agent.

The wetting agent will effect the property of the hydrophobic fibers to which it is applied. Accordingly, these fibers become hydrophilic. Thus it is allowed for any liquid to pass through the top sheet and to be absorbed by the hydrophilic fiber arranged in the intermediate layer 15, which may also be called an absorbent core.

After application of the wetting agent the web 8 is guided into means 25 for cutting out appropriate forms for the final sanitary product. These forms might, e.g., be those illustrated in FIGS. 3 and 4. However, it is also possible to manufacture other forms. After the cut the sanitary product is ready for use.

Figure 5:
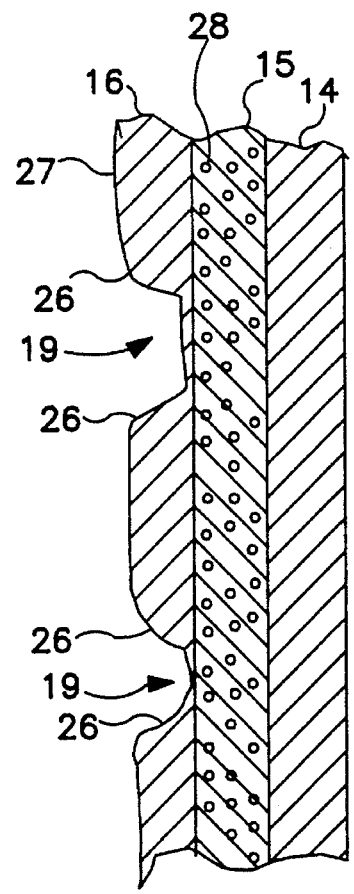

As mentioned earlier it is especially advantages to use an embossing roller 21. As illustrated in FIG. 5 an embossing roller provides the pattern of flow lines 19 in the bottom of grooves 27 formed by the raised ridges of the embossing roller 21. The grooves will direct any liquid directly to the hydrophilic flow lines 19. Thereby the surface 26 of the top sheet 16 which is intended for contact with the user will remain dry. Thereby a high wearing comfort is obtained. Moreover, it is beneficial to use the embossing, seeing that the compressed hydrophilic fibers in the flow lines will be in more intimate contact with each other and the hydrophilic fibers in the intermediate layer 15. Thereby a more efficient liquid guidance is obtained. It could be said that the flow lines act as wicking means, leading any liquid into the intermediate layer.

The intermediate layer 15 may be provided with superabsorbents 28 in order to increase the absorbing capacity. As the outermost layers 14, 16 are liquid impervious, any liquid being transferred to the intermediate layer 15 will remain in that layer. If superabsorbents 28 are used the retaining ability is more efficient. Thus a larger amount of liquid may be absorbed and retained in the intermediate layer 15.

The method to be effected in the plant illustrated in FIG. 2 differs from the above explained in that the means for providing the flow lines are different. In FIG. 2, a series of nozzles 29 are used for applying the wetting agent 30. According to this method the wetting agent is applied to a web which is not mechanically deformed. However, the nozzles 29 may be controlled by a computer 31. Thus, it is possible to make very quick changes in the production. Thus, it is possible to manufacture e.g., diapers for boys and diapers for girls without the need of any mechanical interference in the plant. Moreover, it is possible optionally to provide flow lines over the total area or in selected areas only.

The sanitary product 12, 13 illustrated in FIGS. 3 and 4 represents a child's diaper 12 and a sanitary napkin 13, respectively. In FIGS. 3 and 4, preferred embodiments are shown illustrating that the pattern 17, 18 of flow lines 19 are only provided in selected areas. When the flow lines are provided in selected areas only, it is possible to provide a sanitary product 12, 13 which is specifically manufactured for its specific use. Moreover, the reduced number of flow lines provided in a pre-selected area will reduce the risk of leakage of fluids from the intermediate layer 15.

I claim:

1. A method for production of diapers and sanitary napkins comprising three interconnected layers including a liquid impervious back sheet, a liquid impervious front sheet, and a liquid pervious core, wherein the liquid impervious front sheet and back sheet are made of hydrophobic fibers, the liquid pervious core is made of hydrophilic fibers, and said method includes the steps of providing an embossing roller having a pattern of raised ridges, applying a wetting agent to said raised ridges, and embossing the hydrophobic front sheet with said embossing roller to form a pattern of hydrophilic flow lines by rendering said hydrophobic fibers hydrophilic in said flow lines and provide an intimate contact between hydrophilic fibers in the flow lines and hydrophilic fibers in the liquid pervious core, said wetting agent being applied for neutralizing the hydrophobicity of the fibers in the hydrophobic front sheet and rendering them hydrophilic to thereby provide said pattern of hydrophilic flow lines and enable a liquid flow through the front sheet to the liquid pervious core of hydrophilic fibers.

2. A method as defined in claim 1 wherein the embossing process provides a pattern of grooves, each groove having a bottom, and wherein the hydrophilic flow lines are provided in the bottoms of said grooves.

3. A method as defined in claim 1 wherein the pattern of flow lines is provided only in areas which are intended for a pre-selected position in a final diaper or sanitary napkin.

4. A method as defined in claim 1 wherein superabsorbents are admixed to the hydrophilic fibers provided in the absorbent core.

5. A method as defined in claim 4 wherein the superabsorbents are added only to selected areas of the hydrophilic layer forming the absorbent core.

6. A method as defined in claim 1 wherein diapers and sanitary napkins are manufactured by cutting out appropriate forms of the three interconnected layers.

* * * * *

UNITED STATES PATENT AND TRADEMARK OFFICE
CERTIFICATE OF CORRECTION

PATENT NO. : 5,622,584
DATED : April 22, 1997
INVENTOR(S) : Karl K.K. KROYER

It is certified that error appears in the above-indentified patent and that said Letters Patent is hereby corrected as shown below:

ON THE TITLE PAGE:

[76] Inventor: Karl K.K. Kroyer, deceased, late of Le View Moulin France

[73] Assignees (Heirs): Ingelise Kobs Krøyer, Le View Moulin, 12 vue de la Liberation, F-06520 Magagnosc, France Vibeke Kobs Houlberg Borgerdiget Herleu, Denmark Signed and Sealed this Second Day of September, 1997

Attest:

BRUCE LEHMAN

Attesting Officer

Commissioner of Patents and Trademarks